(12) United States Patent
Funke

(10) Patent No.: US 8,371,621 B2
(45) Date of Patent: Feb. 12, 2013

(54) FITTING CONNECTION

(76) Inventor: Herbert Funke, Pfaffenhofen/Glonn (DE)

( * ) Notice: Subject to any disclaimer, the term of this patent is extended or adjusted under 35 U.S.C. 154(b) by 178 days.

(21) Appl. No.: 12/821,553

(22) Filed: Jun. 23, 2010

(65) Prior Publication Data

US 2010/0327577 A1 Dec. 30, 2010

(30) Foreign Application Priority Data

Jun. 25, 2009 (EP) .................................. 09008332

(51) Int. Cl.
*F16L 19/06* (2006.01)

(52) U.S. Cl. ........................................ 285/342; 285/249
(58) Field of Classification Search ................. 285/249, 285/342, 343
See application file for complete search history.

(56) References Cited

U.S. PATENT DOCUMENTS

| | | | |
|---|---|---|---|
| 3,150,517 A | | 9/1964 | Kuffer et al. |
| 3,748,833 A | | 7/1973 | Karas et al. |
| 3,800,602 A | | 4/1974 | Jones |
| 3,973,792 A | | 8/1976 | Gonner |
| 4,394,263 A | * | 7/1983 | Dosch et al. ............... 210/198.2 |
| 4,776,618 A | * | 10/1988 | Barree ........................ 285/342 |
| 4,787,656 A | * | 11/1988 | Ryder .......................... 285/342 |
| 5,288,113 A | * | 2/1994 | Silvis et al. ................... 285/342 |
| 5,494,641 A | * | 2/1996 | Krstanovic ................... 285/342 |
| 5,744,100 A | * | 4/1998 | Krstanovic ................... 285/343 |
| 6,200,113 B1 | * | 3/2001 | Van Davelaar ............... 285/343 |
| 6,260,890 B1 | * | 7/2001 | Mason ......................... 285/332 |
| 6,267,143 B1 | * | 7/2001 | Schick ....................... 285/124.3 |
| 6,709,027 B2 | * | 3/2004 | Rittenhouse ................. 285/332 |
| 7,472,928 B2 | * | 1/2009 | Salven et al. ................ 285/342 |
| 7,681,926 B2 | * | 3/2010 | Valaskovic et al. .......... 285/342 |
| 7,909,367 B2 | * | 3/2011 | Plant et al. .................. 285/342 |

FOREIGN PATENT DOCUMENTS

| | | |
|---|---|---|
| DE | 20 2005 011825 U1 | 11/2006 |
| EP | 0 225 779 A | 6/1987 |
| EP | 0 586 237 A | 3/1994 |
| EP | 1 443 330 A | 8/2004 |
| GB | 646 788 A | 11/1950 |
| GB | 2 172 073 A | 9/1986 |
| WO | 02/39105 A1 | 5/2002 |
| WO | 2007/012445 A2 | 2/2007 |
| WO | 2009/024171 A1 | 2/2009 |

OTHER PUBLICATIONS

European Search Report, EP09008332.0-2204, mailed Mar. 31, 2010.

* cited by examiner

*Primary Examiner* — David E Bochna
(74) *Attorney, Agent, or Firm* — Ziegler IP Law Group, LLC

(57) ABSTRACT

A fitting connection for a capillary has a sealing bushing, a compression bushing, and a backing bushing. The backing bushing has a bore for receiving the sealing bushing and the compression bushing into the backing bushing, and the sealing bushing and the compression bushing are each provided with a central bore for feeding through a capillary tube. The bore of the backing bushing has a partly slightly conical bore end which compacts the sealing bushing such that the bore of the sealing bushing exerts a radial surface pressure onto the external wall of the capillary.

3 Claims, 6 Drawing Sheets

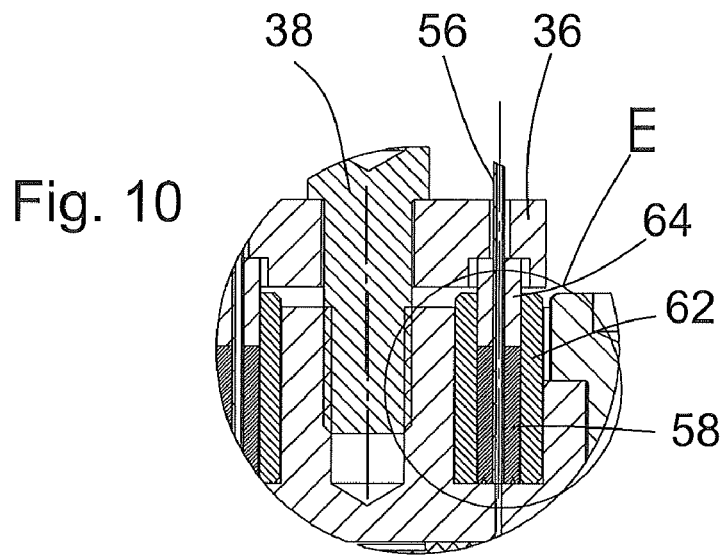
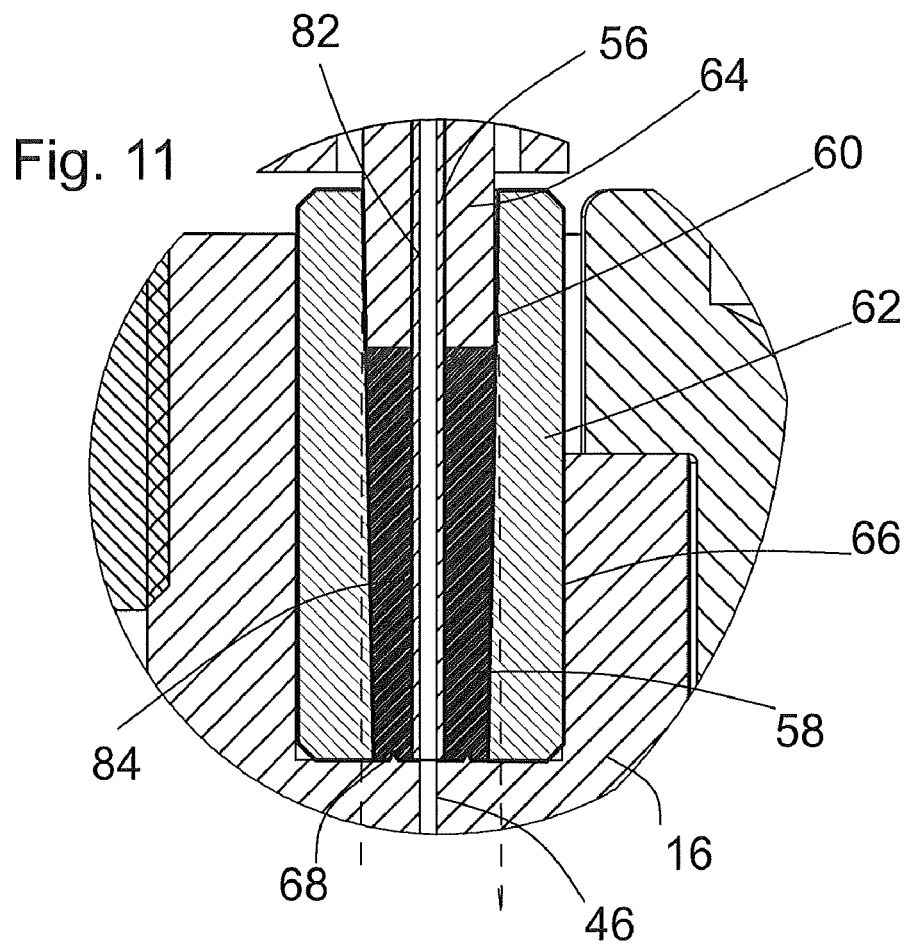

FITTING CONNECTION

BACKGROUND

1. Field

The disclosed embodiments relate to a fitting connection for a capillary adapted for use in high-performance liquid chromatography (HPLE) or capillary electrophoresis (CE).

2. Brief Description of Related Developments

The Document WO 02/39105 discloses a sample injection valve for high-performance liquid chromatography (HPLC) devices comprising a stator plate with inlet ports for the analyte solution and with connections at both ends of a sample loop. Moreover, the valve features a movable part in the form of a rotor disk with connecting channels provided within the rotor disc. The rotor disk may be moved by a handle or motor/gear actuator in order to bring the ends of the connecting channels into flush position with respective bores in the stator plate such that the connecting channels may be moved into a sample loading position in which the connecting channel is connected to the sample inlet and to the sample outlet ports, and into a sample injecting position in which the connection channel is connected to the sample loop duct.

Sample injection valves with rotor-type movable bodies are comparatively large and are essentially limited to single-channel HPLC/chemical analysis applications. Multi-channel applications require multiple rotor valves and respective actuators associated in parallel, which design entails a cost intensive and complex implementation, specifically since the available installation space is limited by the distance between the rows of wells in a well plate typically utilised for storing and supplying the analyte solutions.

Known fitting connections for use in such high-pressure applications have turned out to be too large to be used for all liquid connections of the apparatus according to the aspects of the disclosed embodiments, in particular because the size of the valves is continuously reducing.

SUMMARY

It would be advantageous to provide small-size fitting connection for use in high pressure applications such as for the sample injection when performing HPLC and CE applications, specifically in conjunction with high sample throughput (HST) methods.

One aspect of the disclosed embodiments relates to a fitting connection for a capillary comprising a polymer sealing bushing, a compression bushing and a backing bushing with the latter components preferably made from stainless steel or titanium. The fitting connection may in particular be used in connection with fused silica capillaries. The fitting connection is especially adapted to the small mounting space available in the apparatus described above. Specific constraints on the distance between the fitting connections are imposed by the distance pattern of the wells containing the sample solutions in the well plates. Complying with these constraints facilitates the use of commercially available standard well plates. However, standard fitting connections may be used, e.g., at the pure solvent/buffer supply ports in the bottom stator plate.

Preferably, a liquid connecting assembly features an inert metallic backing bushing e.g. made of stainless steel or titanium and a (polymer) sealing bushing with the latter component pressed into said backing bushing in such way that a flat front face is formed which shape avoids any dead volume between said front side and the bottom of the pertinent receiving bore for said connecting assembly in one of the stator plates when being liquid tightly mounted/pressed into these bores.

The liquid connection assembly comprising the backing bushing, the sealing bushing and the compression bushing is preferably fixedly mounted by means of a buckle element featuring either a single or a dual wing depending on fixedly mounting either one or two liquid connections, with said element exerting only axial and no torsion compression forces.

In the fitting connection according to the aspects of the disclosed embodiments, the backing bushing has a common bore for the sealing bushing and the compression bushing into the backing bushing. The section of said bore receiving the sealing bushing has a slightly conical shape for achieving a press-fit by squeeze ramming.

The sealing bushing and the compression bushing are each provided with central bores for feeding through the pertinent fluid connection capillary.

The sealing bushing may preferably be made of polytetrafluoroethylene (PTFE).

The PTFE surface may preferably contact the external wall of the capillary end within the entire contact area. The sealing element may preferably be entirely made of PTFE.

Further characterising features and the advantages thereof may be found in the following description of the disclosed embodiments. The description, the Figures and the claims contain multiple features in particular combinations. The skilled person may easily find other combinations or sub-combinations of the features without departing from the scope of the invention as set out in the independent claims.

BRIEF DESCRIPTION OF THE DRAWINGS

FIG. 10 is a view of the detail D in FIG. 9, FIG. 11 is a view of the detail E in FIG. 10.

DETAILED DESCRIPTION OF THE DISCLOSED EMBODIMENTS

Figure 1:
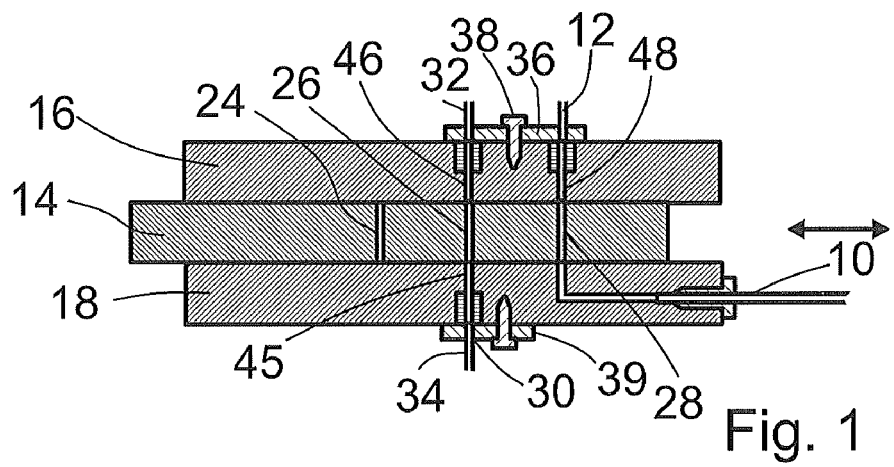
FIG. 1 is a schematic illustration of an apparatus for proportionating, injecting and routing analyte sample solutions according to the aspects of the disclosed embodiments in a loading position.

FIG. 1 is a schematic illustration of an apparatus for proportionating, injecting and routing analyte sample solutions in microlitre or nanolitre scale into high pressure fluid streams. In most applications, the fluid stream is routed from a solvent supply connection 10 to a connection 12 which is fluidicly connected e.g. to a liquid chromatography or directly a detector system (not shown).

The solvent supply connection 10 is connected to a high pressure solvent/buffer solution delivery system whereby the filling stroke's liquid composition may be controlled by solenoids for forming low pressure side gradients (not shown).

The apparatus comprises the slider plate 14 of the apparatus. The slider plate 14 is sandwiched between a top stator plate 16 and a bottom stator plate 18 in such a way that a linear back and forth sliding motion is enabled in the two directions indicated with the double arrow in FIGS. 1 and 2.

Figure 2:
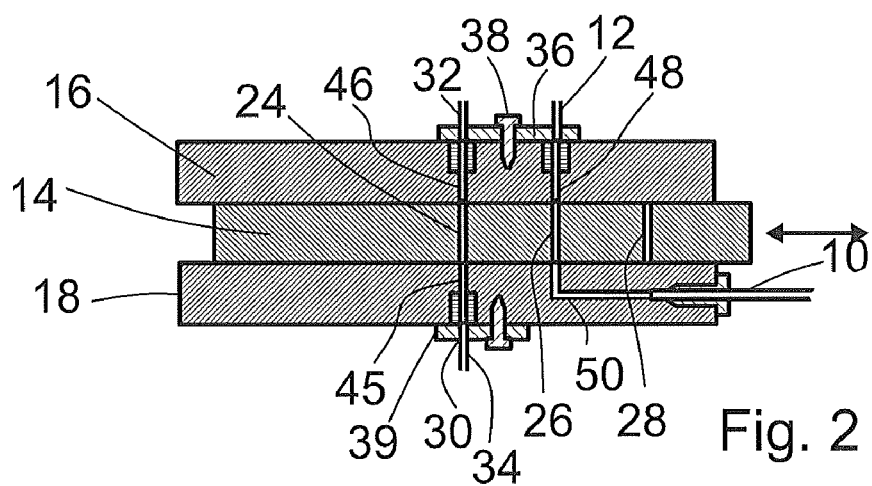
FIG. 2 is a schematic illustration of the apparatus according to FIG. 1 in a injecting position.
Figure 3:
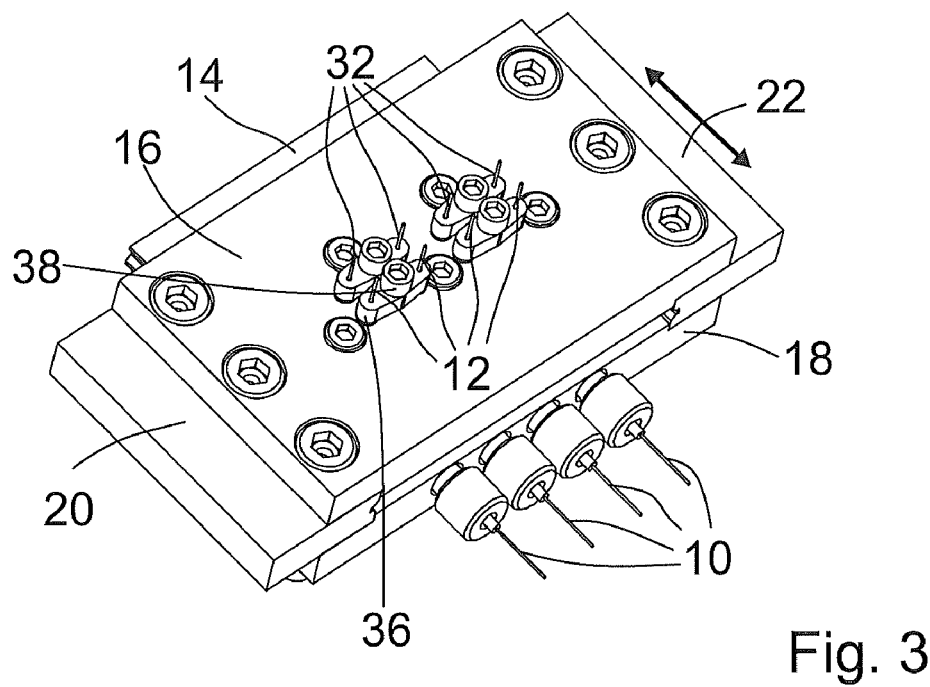
FIG. 3 is a perspective view on the apparatus according to FIGS. 1 and 2.
Figure 4:
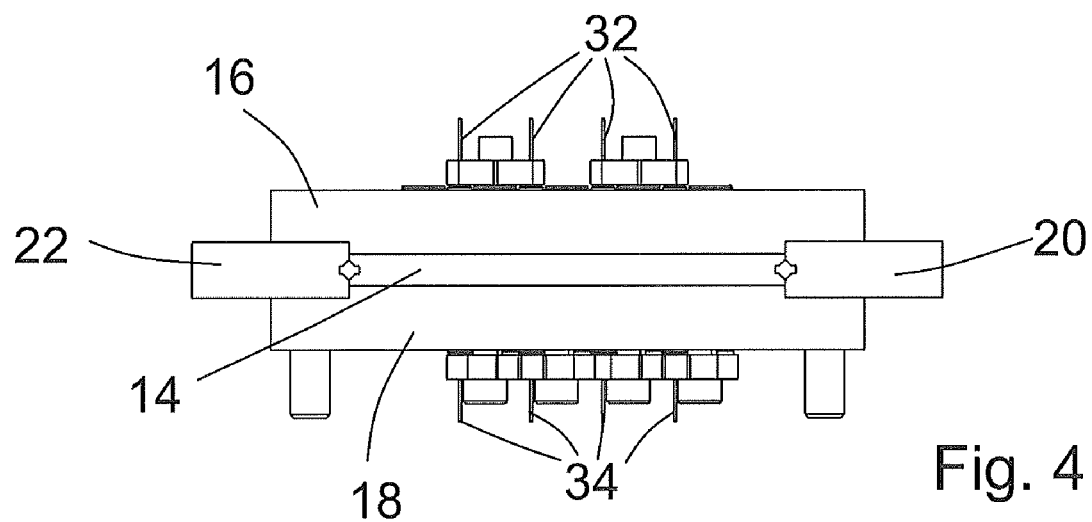
FIG. 4 is a side view of the apparatus according to FIGS. 1 to 3.

For a mechanically precision alignment during motion of the slider plate 14, the slider plate 14 is guided by means of two lateral guiding bars 20, 22 illustrated in FIG. 3. The motion of the slider plate 14 is effected by an actuator (not shown) which is configured to move the slider plate 14 from a sample loading position shown in FIG. 1 to a sample injecting position shown in FIG. 2.

The slider plate 14 is fitted with parallel rows of micro bores, each row comprising three bores 24, 26, 28. The three bores 24, 26, 28 have a diameter of e.g. 200 µm and are exactly aligned in a row with the row axis being congruent with the slider plate's motion axis 14.

In the sample loading position illustrated in FIG. 1, the central bore 26 of each row connects a sample intake connection 30 in the bottom stator plate 18 with a sample taking up connection 32 in the top stator plate 16. The sample taking up connection 32 is connected to a precision micro syringe (not shown) or to an alternatively suitable precision metering device. The sample intake connection 30 is a fitting connection bearing an intake nozzle 34 which may be immersed into the analyte solution in a well of a well plate (not shown) An aliquot of the sample solution is taken up into the sample bore 26. The volume of the sample aliquot equals to the volume of the central bore 26 and it is determined by the diameter and length of the bore 26.

Subsequent to complete filling of the bore 26 with the analyte solution, the slider plate 14 is moved into the sample injection position as illustrated in FIG. 2, in which position the loaded sample solution aliquot is injected into the high pressure fluid stream conveyed from connection 10 to connection 12 of the apparatus. In the sample injection position, the analyte solution aliquot is carried with the high pressure fluid stream and subsequently the sample bore 26 is filled with pure solvent/buffer solution fed from the pertinent delivery system. In the sample loading position (FIG. 1), the bore 28 on FIGS. 1 and 2 connects the connections 10 and 12, whereas the bore 24 connects the sample loading connection and the intake connection 32 in the sample injection position.

Each of the connections 10 is a standard fitting connection for standard 1/16" outside diameter tubing, the connections 12, 32 and 34 a fitting connection for a fused silica capillary line with the capillary exhibiting a typical outer diameter of 360 µm and an inner diameter of e.g. 200 µm. The liquid channel connecting the sample intake nozzle 34 and the sample injection connection 32 represent the proportionating range of the sample loading liquid duct system and the channel connecting the solvent supply connection 10 and the outlet connection 12 represents the main fluid stream liquid duct system.

When the slider is being shifted into the sample loading position for sample solution intake, the central bore 26 in the slider plate 14 functions as a liquid duct between the sample intake bore 45 in the bottom stator plate and the sample solution discharge bore 46 in the top stator plate 16. In the sample injecting position, the central bore 26 in the slider plate 14 is aligned with a sample solution discharge bore 48 in the top stator plate and with a solvent supply bore 50 in the bottom stator.

FIG. 3 shows a perspective view of the apparatus design described above. The four rows of bores in the slider plate 14 are arranged at positions corresponding to the positions of the four inlet connections 10 in the bottom stator plate 18. The distance between the rows of bores to the fluidicly corresponding rows of inlet connections 10 and the fluidicly corresponding outlet connections 32 is twice the distance of rows of wells wherein the sample solutions are stored on a standard well plate. The typical raster measure of standard well plates is 4.5 mm, entailing that the distance between the parallel rows of the bores 24, 26, 28 (cf. FIG. 12) is 9 mm. The slider plate 14 is preferably made of engineering ceramics, specifically zirconia. The top stator plate 16 and the bottom stator plate 18 are made of PEEK.

The outlet connections 12 and 32 in the top stator plate 14 are particular fitting connections described in more detail below. The connections are held by a double-wing buckle 36 fixed with a central tensioning screw 38. The connection 10 is a standard fitting connection. The sample intake connection is a special fitting connection similar to the connections 12 and 32 at the top stator plate 16 but is combined only with the single-wing buckle 39. With both liquid connection types said wing buckle design exerts only axial and no twisting tensioning forces.

The double-wing buckles 36 tightened with tensioning screws 38 at the top stator plate 16 are each used to tighten a pair of outlet connections 12, 32 representing adjacent rows of liquid channels within the apparatus.

Figure 5:
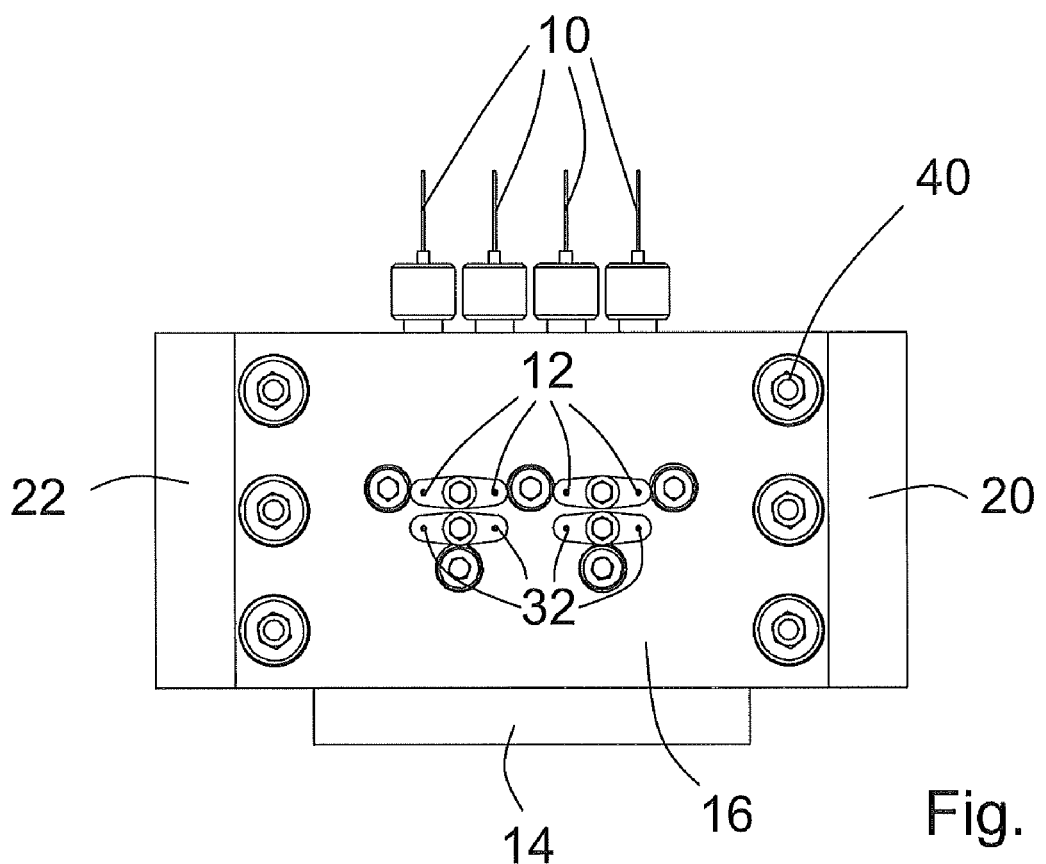
FIG. 5 is a top view of the apparatus according to FIGS. 1 to 4 from above.
Figure 6:
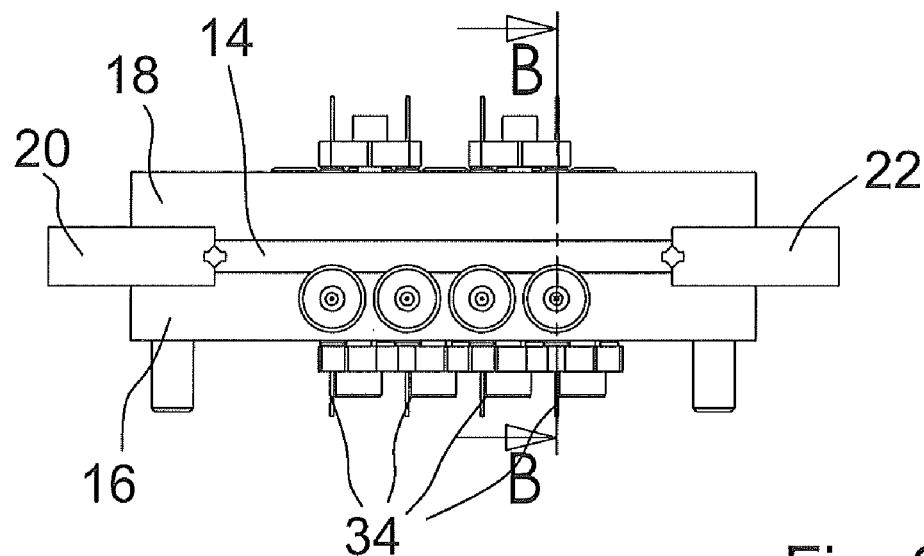
FIG. 6 is a view of the apparatus according to FIGS. 1 to 5 from aside.

FIG. 5 is a top view of the apparatus showing six screws 40 compressing the top stator plate 16, the bottom stator plate 18 and the lateral guiding bars 20, 22 to a sandwiched stack. Further screws 42 are used to generate an over the active area evenly effective defined preloading of the stack-structure according to the aspects of the disclosed embodiments comprising the top stator plate 16, the bottom stator plate 18 and the slider plate 14. The preloading may be affected e.g. by using spring disks or undulated springs (not shown).

Figure 12:
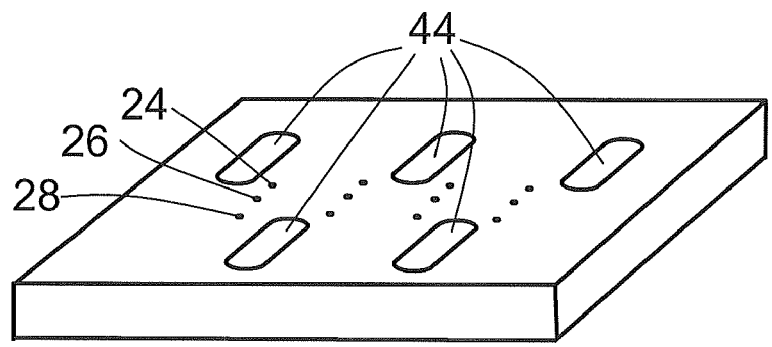
FIG. 12 is a perspective view of a slider plate of the apparatus.

Each of the preloading screws 42 is fed through one of five arranged slot holes 44 arranged in parallel in the slider plate 14 as illustrated in FIG. 12. The slot holes 44 are arranged in parallel to the shifting direction of the slider plate for establishing a fluid connection between the top stator plate 16 and the bottom stator plate 18 through the pertinent bores in the slider plate 14.

The provision of the preloading screws 42 enables the generation of a uniformly distributed preloading at the interface areas between the top stator plate 16 and the base stator plate 18 on the one hand and the slider plate 14 on the other hand. The preloading is as such that at the interface areas liquid-tightness is achieved between plates 14, 16 and 18 preventing lateral and/or cross-over leakage even at high pressures of up to 70 bar occurring during analysis operation.

Figure 7:
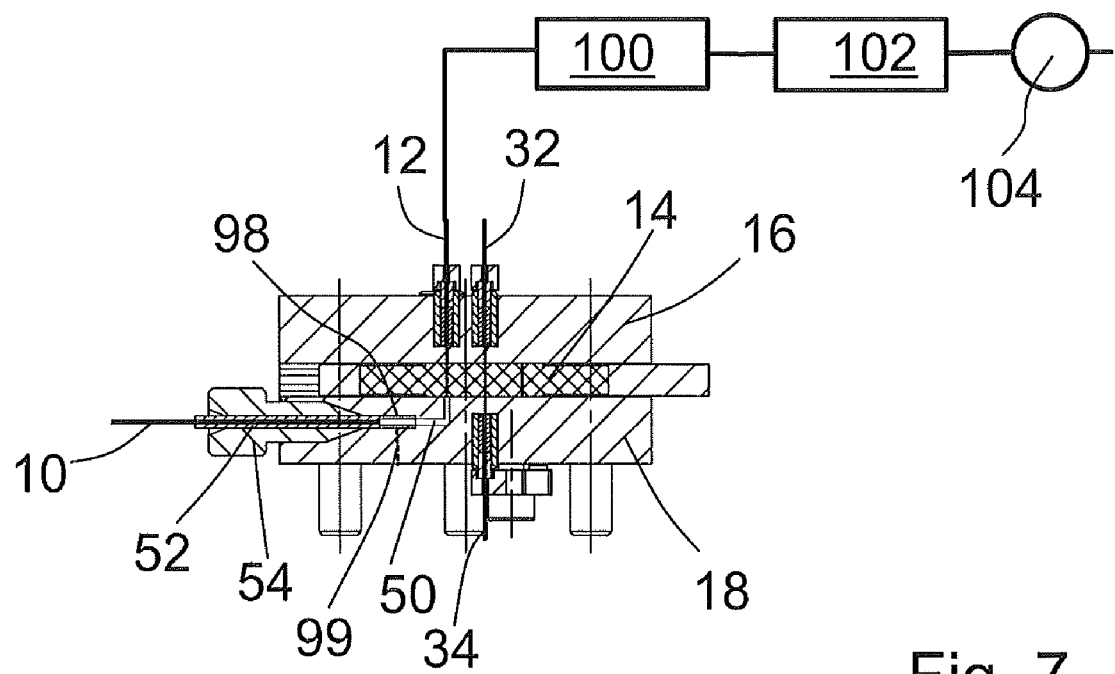
FIG. 7 is the section along the line B-B in FIG. 6.
Figure 8:
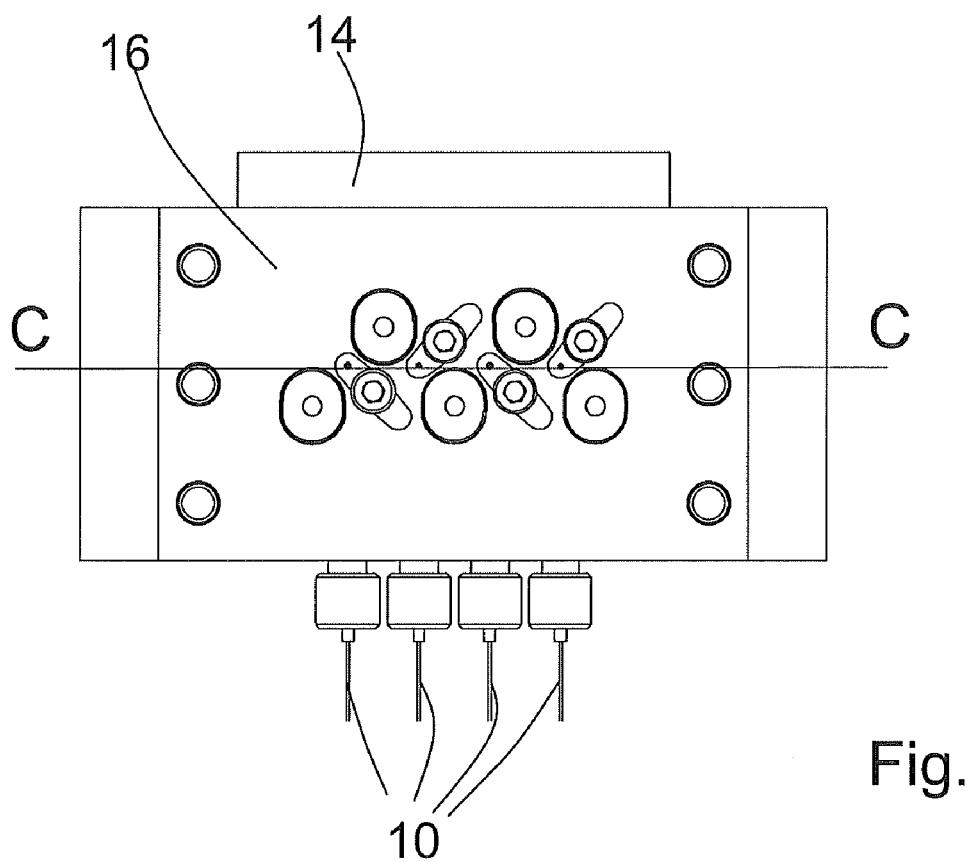
FIG. 8 is a view of the apparatus according to FIGS. 1 to 7 from below.
Figure 9:
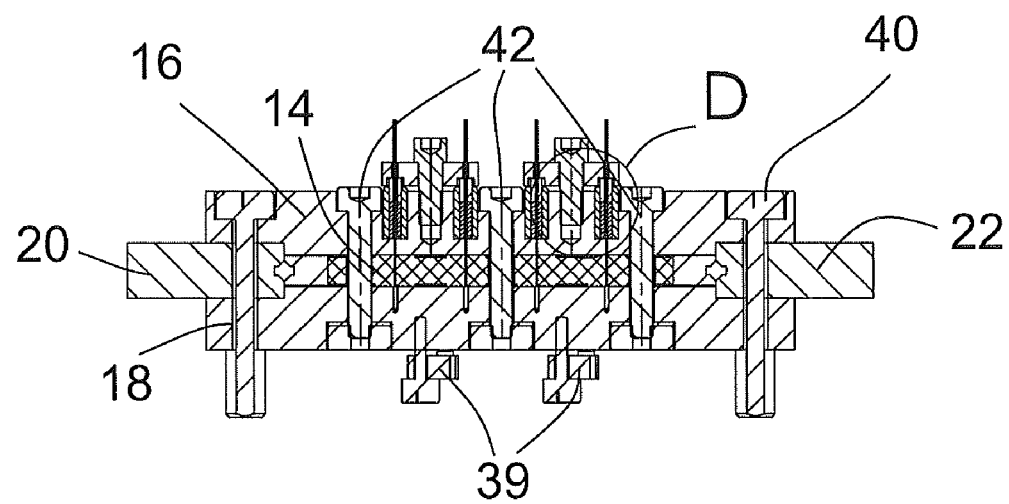
FIG. 9 is a cross-sectional view of the apparatus along the line C-C in FIG. 8.

As shown in FIG. 7, for coping with the machining of the given aspect ratio the solvent supply bore 50 has a larger diameter than the diameter of the application critical micro bores wetted by the analyte solution. The solvent supply bore 50 empties into an elbow duct allowing a liquid connection to the solvent supply connection 10 in lateral configuration to the bottom stator plate 18 by means of a standard fitting which may be fitted with a sleeve 52 as adapter bushing 54 for the case that e.g. fused silica capillaries are foreseen to establish the pertinent fluidic line.

The non-standard fitting connections employed in the disclosed embodiments are illustrated in more detail with reference to FIG. 10 and FIG. 11. A capillary tube 56 is inserted into a polymer sealing bushing 58, preferably made of polytetrafluorethylen (PTFE) and pressed into the central bore 60 of a metallic backing bushing 62, preferably made of stainless steel or titanium by means of a again metallic compression bushing 64. The capillary tube 56 is fed through central bores 82, 84 of the essentially cylindrical compression bushing 64 and sealing bushing respectively. The compression force exerted by the compression bushing 64 onto the sealing bushing 58 is generated by the double-wing buckle 36 or the single-wing buckle 39 fixed/set by the screw 38 described above.

The backing bushing 62 features a receiving bore 60 which diameter exhibits a conical shape towards the front end. Consequently, when the connection is being set, the sealing bushing 58 is compacted and thus exerting a radial surface sealing force onto the mantle of the capillary tube 56 along the contact section of the mantle of the capillary tube 56 and the radially inner surface of the bore 84. It is important to note that by avoiding line-contact only, the sealing force acts in a gradual mode along the entire contact surface of the capillary.

The backing bushing 62 is pressed mounted into a corresponding receiving bore 66 in the top stator plate 16 or the bottom stator plate 18. In the centre of said receiving bore 66, the capillary tube 56 is adjusted with the respective bore 45, 46, 48 in the top or bottom stator plate 16, 18, with the inner diameter essentially corresponding to the inner diameter of the capillary tube 56. The bottom of the receiving bore 66 features a contour with a liquid tightness enhancing sealing structure 68, e.g. an annularly raised or alternatively, grooved profile, with dimensionally designed for proper interacting with the end face of the sealing bushing 58.

With the liquid connection being mounted, the capillary tube 56 and the sealing bushing 58 form a functional assembly with its properly straightened front side bottoming within the receiving bore 66, avoiding clearance/dead volume within the interface area.

The apparatus according to the aspects of the disclosed embodiments is operated in such a way that the stack with the stator plates 16, 18 is held stationary while the well plate is positioned by means of a movable support device enabling a horizontal and vertical positioning of the well plate in order to select the analyte solutions to be injected into the analytical system. With a distance of two wells, the apparatus according to the aspects of the disclosed embodiments enables the parallel intake of analyte solution aliquots from four wells arranged in one row on a well plate.

Filling one or more of the wells on the well plate with pure solvent/buffer solution facilitates an online cleaning/flushing of the capillary intake nozzle tube 34.

Subsequently to injecting a sample solution aliquot, for an external cleaning of the sample intake nozzle tube, the tip of the capillary nozzle tube is repeatedly immersed into one or more well(s) containing pure solvent. For performing a cycle of internal flushing of the proportionating channel, a certain volume of pure solvent is drawn in and discharged to waste wells.

Subsequent to injecting a sample solution aliquot, as well as for an external cleaning of the sample intake nozzle tube, the tip of the capillary nozzle tube is repeatedly immersed into one or more well(s) containing pure solvent.

For performing a cycle to internally flush the proportionating channel, a certain volume of pure solvent is drawn in and subsequently discharged to waste wells.

Figure 13:
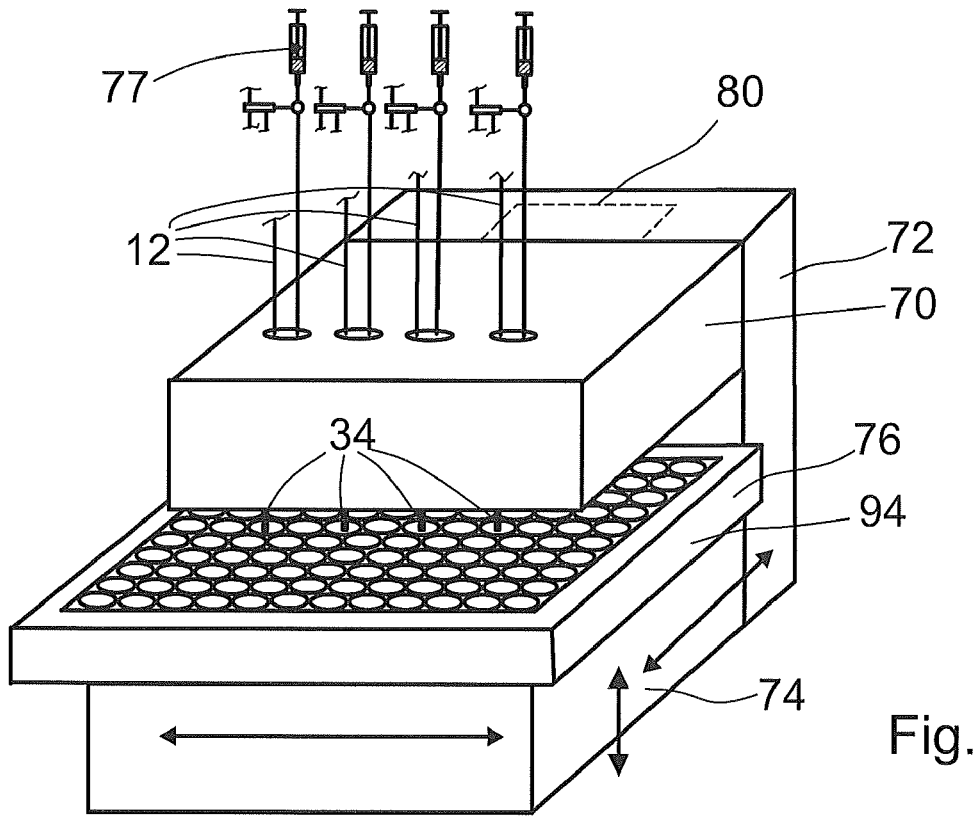
FIG. 13 is a perspective view of a four-channel parallel sample injecting system with the apparatus for proportionating, injecting and routing analyte sample solutions with a well plate, with a well plate manipulator, and with a delivery system for intaking and/or discharging liquids and/or gas for each channel.

The flexibility of the assembly may be upgraded by engaging 1+n well plates alternately made accessible by the pertinent well plate tray system 74 (FIG. 13).

FIG. 12 is a schematic representation of the slider plate 14 employed in the apparatus according to the aspects of the disclosed embodiments. The slider plate is provided with five slot holes 44 and twelve micro bores arranged in four rows featuring three bores each The slider plate 14 is made from engineering ceramics and the bores therein are machined prior to firing the blank piece and anticipating a slightly individual shrinkage. The bores' accurate volumetric size, which determines the sample volume, is assessed by an initial calibration run performed under actual analysis conditions. As it is of utmost importance that the sample bore 26 and the bores 50 and 48 in the top stator plate 16 and the bottom stator plate 18 can be moved to precise flush position for sample injection (FIG. 2), said bores 48, 50 may be machined to comply with the actually precision-measured position of the sample bore 26. The same applies for bores 45, 46 in the top stator plate and for bores 16, 18 in the bottom stator plate.

FIG. 13 is a perspective view of a four-channel parallel sample injecting system with the apparatus for proportionating, injecting and routing analyte sample solutions according to the aspects of the disclosed embodiments, with a well plate, with a well plate manipulator, and with a delivery system for each channel. The stack of plates is arranged in a housing 70 with a pedestal 72 supporting the apparatus in a stationary position, with the sample intake tube nozzles 34 held above a well plate manipulator 74 being equipped with three linear motors for moving a well plate 76 placed on an auxiliary tray 94 arranged on the well plate manipulator 74 in the x- y- or z-direction. The well plate manipulator 74 serves as a moveable support device for the well plate 76. By moving the well plate 76, the four intake tube nozzles 34 may be simultaneously immersed in a set of four wells. Sets of wells to be simultaneously served represent wells located in one row with a distance of two wells. An actuator 80 for positioning the slider plate 14 is arranged in the housing 70 and in the pedestal 72.

Figure 14:
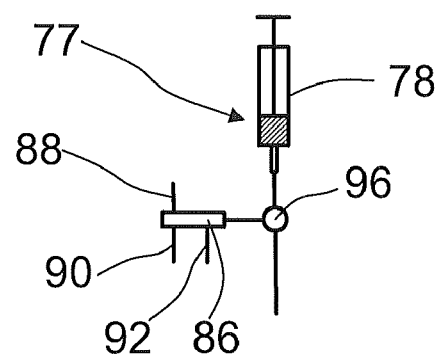
FIG. 14 is an illustration of one of the delivery systems for intaking and/or discharging liquids and/or gas in FIG. 13.

The sample intake connections or outlet connections 32 in the top stator plate are connected to respective delivery systems 77 and/or a manifold 86 with solenoids connecting liquid and/or gas lines 88, 90, 92 to a microsyringe 78 via a switching valve 96 (FIG. 14).

FIG. 14 is an illustration of one of the delivery systems 77 FIG. 13 in greater detail. A micro syringe 78 can be connected via a solenoid array 86 to either the connection 32 or to one out of three different liquid and/or gas lines 88, 90, 92. The line 88 may be used e.g. for supplying $N_2$ to the system, the lines 90 and 92 may be used for supplying liquid media according to the specific analysis requirements to the system.

The connections 12 are used for connecting the parallel sample injecting system to a chromatography column each or directly to a multi-channel detector system.

| 10 | solvent supply connection |
|----|---------------------------|
| 12 | Connection |
| 14 | slider plate |
| 16 | stator plate |
| 18 | stator plate |
| 24 | Bore |
| 26 | Bore |

| | |
|---|---|
| 28 | Bore |
| 30 | sample intake connection |
| 32 | Connection |
| 34 | Nozzle |
| 36 | buckle (dual wing) |
| 38 | Screw |
| 39 | buckle (single wing) |
| 42 | preloading screw |
| 44 | slot hole notch |
| 45 | Bore |
| 46 | Bore |
| 48 | Bore |
| 50 | solvent supply bore |
| 52 | Sleeve |
| 54 | Bushing |
| 56 | capillary tube |
| 58 | Bushing |
| 60 | Bore |
| 62 | backing bushing |
| 64 | compression bushing |
| 66 | receiving bore |
| 68 | sealing structure |
| 70 | Housing |
| 72 | Pedestal |
| 74 | Manipulator |
| 76 | well plate |
| 77 | delivery system |
| 78 | micro syringe |
| 80 | Actuator |
| 82 | Bore |
| 84 | Bore |
| 86 | solenoid manifold |
| 88 | Connection |
| 90 | Connection |
| 92 | Connection |
| 94 | Tray |
| 96 | switching valve |

What is claimed is:

1. A fitting connection for a capillary comprising:
a tubular sealing bushing, a compression bushing and a backing bushing, the backing bushing having a bore for receiving the sealing bushing and the compression bushing such that the sealing bushing is completely inserted into the bore and backed by an inner wall of the bore, the sealing bushing and the compression bushing being each provided with a central bore for feeding through a capillary tube,
wherein an end of the bore of the backing bushing has a partly slightly conical shape for compressing the sealing bushing such that an inner wall of the central bore of the sealing bushing exerts a surface pressure in a radial direction onto an external wall of a capillary end within a contact area between the external wall of the capillary and an inside surface of the central bore,
wherein, by being pressed into a receiving bore in a stator plate, the fitting connection further comprises an assembly comprising the backing bushing and the sealing bushing pressed into said backing bushing, wherein said assembly includes a flat frontal surface avoiding a dead volume in an interface area between the front face and a bottom of the receiving bore, and
wherein said flat front face of the assembly is formed by flush front faces of the backing bushing, the capillary and the sealing bushing abutting with a bottom of the receiving bore, respectively.

2. The fitting connection according to claim 1, wherein an assembly comprising the compression bushing, the backing bushing and the sealing bushing is fixed by means of a single or dual wing buckle element, wherein said buckle element exerts an axial pressure onto said compression bushing, wherein said axial pressure is transferred by the compression bushing onto the sealing bushing for achieving the compression of the sealing bushing such that only axial and no torsion compression forces are exerted onto the assembly.

3. The fitting connection according to claim 1, wherein the sealing bushing comprises sealing surfaces of polytetrafluorethylene (PTFE).

* * * * *